United States Patent [19]

Peters

[11] 4,381,669

[45] May 3, 1983

[54] METHOD AND APPARATUS FOR DETERMINING THE NUMBER OF SEEDS PER UNIT WEIGHT IN A SEED SAMPLE

[76] Inventor: Roger L. Peters, 3080 N. Leutz, Oak Harbor, Ohio 43449

[21] Appl. No.: 226,009

[22] Filed: Jan. 19, 1981

[51] Int. Cl.³ .......................................... G01N 15/02
[52] U.S. Cl. ............................... 73/432 PS; 209/237
[58] Field of Search .......................... 73/432 PS, 433; 209/237, 239, 680, 682

[56] References Cited

U.S. PATENT DOCUMENTS

| | | | |
|---|---|---|---|
| 1,120,012 | 12/1914 | Bell | 209/237 |
| 1,445,957 | 2/1923 | Junkin | 209/680 |
| 2,782,926 | 2/1957 | Saxe | 73/432 PS X |
| 3,977,525 | 8/1976 | Lamborn | 209/682 X |

OTHER PUBLICATIONS

R. D. Cadle-*Particle Size Determination*-Interscience Publishers, Inc. New York, 1955, pp. 175-196.
J. Dasher-Information Circular 7224, Bureau of Mines, Nov. 1942, pp. 2-3.

*Primary Examiner*—Charles A. Ruehl
*Attorney, Agent, or Firm*—Wilson, Fraser, Barker & Clemens

[57] ABSTRACT

The correct plant population is obtained by utilizing a method and apparatus for determining the number of seeds per unit weight in a sample number of seeds representative of the type of seeds to be planted. A seed sorter comprising a plurality of stacked sieves is utilized to sort the sample into groups according to seed size. Each group can then be individually weighed to obtain a weight which is multiplied by an associated constant representing the average number of seeds per unit weight for the size range. The product is the average number of seeds per sieve which numbers are totalled and divided by the sample weight to obtain the average number of seeds per unit weight. If no weighing scale is available, the user can individually count the number of seeds in each group and divide by the associated constant to obtain the weight per size range for the sample. The weights are added and divided into the total number of seeds in the sample to obtain the average number of seeds per unit weight. Each of the sieves is generally cylindrical in shape with an open top and an apertured bottom wall. A cup-shaped bottom below the bottom one of the sieves receives material small enough to pass through the apertures in the bottom sieve and a lid is releasably attached at the open top of the uppermost sieve by a generally U-shaped wire closure means.

8 Claims, 4 Drawing Figures

METHOD AND APPARATUS FOR DETERMINING THE NUMBER OF SEEDS PER UNIT WEIGHT IN A SEED SAMPLE

BACKGROUND OF THE INVENTION

It is well known in the agricultural area that, in order to obtain an optimum crop yield, it is desirious to plant a predetermined number of seeds per acre. Under-population will typically result in decreased yields, while over-population results in increased seed costs, barren and weak stalks, and decreased yields.

The desired plant population is determined by the type and variety of plants to be planted, row width, plant spacing, etc. For example, soybean varieties typically fall into the following three catagories: (1) indeterminate (tall plants), (2) determinate (semi-dwarf plants), and (3) semi-determinate (bush-type plants). Each requires a different plant poplulation per acre in order to obtain the optimum yield.

SUMMARY OF THE INVENTION

The present invention relates to a method and apparatus for determining the number of seeds per unit weight in a sample of seeds representative of a larger number of seeds. By knowing the average number of seeds per unit weight, a farmer is able to maintain the correct plant population during the seeding operation.

According to the present invention, a seed sorter comprising a plurality of stacked sieves is utilized to sort the sample into groups according to seed size. After the seeds have been sorted, the user can utilize one of two methods to determine the average number of seeds per unit weight, depending on whether a weighing scale is available to the user.

If a weighing scale is available, the seeds from each sieve are then multiplied by a respective one of a group of predetermined constants to obtain a product representing the average number per unit weight of seeds having a particular group size. All of these products are then toatalled to obtain the average number of seeds per unit weight. Each constant represents the average number of seeds per unit weight (typically one pound) which are of a size to be retained by an associated sieve.

If no weighing scale is available, the user can use a hand count method. According to this method, the user individually counts the number of seeds which are found in each sieve. Next, each of these counts is divided by the respective one of the above-mentioned predetermined constants representing the average number per unit weight of seeds having a particular group size. The resulting quotients each represent the weight of the respective group of seeds. These weights are then totalled to obtain the total sample weight. Dividing the total number of seeds in the sample by the sample weight results in a value representative of the average number of seeds per unit weight.

Accordingly, it is an object of the present invention to provide a method and an apparatus for determining the average number of seeds per unit weight of a sample of seeds to increase crop yield and decrease seed cost.

DESCRIPTION OF THE PREFERRED EMBODIMENT

Figure 1:
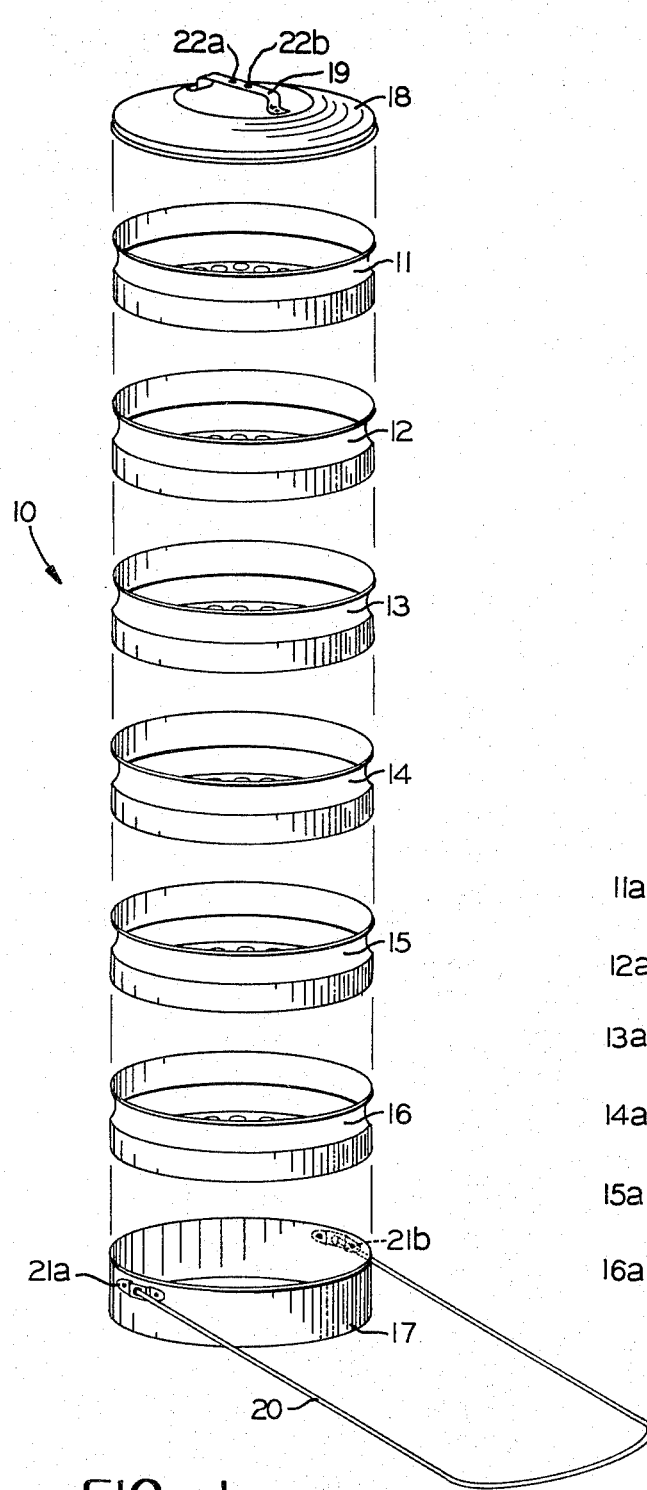
FIG. 1 is an exploded perspective view of a seed sorter utilized to carry out the method of the present invention.

The first step involved in the method according to the present invention is to sort by size a sample of seeds representative of a larger number of seeds which are to be planted. There is shown in FIGS. 1 through 4 a seed sorter 10 which can be utilized to sort a grain sample according to seed size. The sorter 10 includes a plurality of individual sieves 11 through 16 which are oriented in a stacked arrangement over a cup shaped bottom 17. A top lid 18 having a handle 19 is used to cover the open top of the uppermost sieve 11.

The sieves 11 through 16 are maintained in stacked arrangement by a generally U-shaped wire closure 20 having opposite ends which are hingedly attached to the bottom 17 by brackets 21a and 21b. The closure 20 is designed to slide over the top of the handle 19. A pair of raised portions 22a and 22b cooperate to form a groove for receiving a central portion of the wire closure 20.

Figure 3:
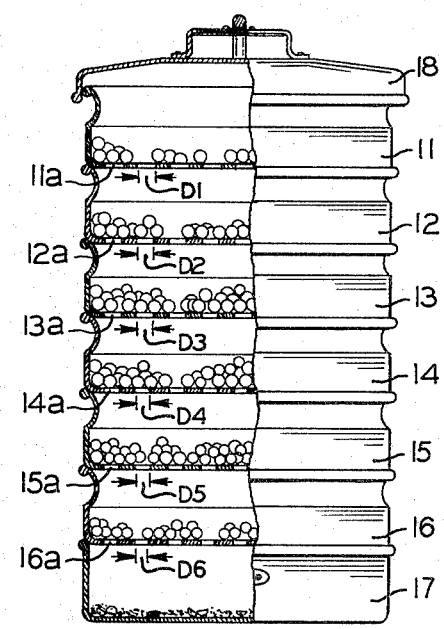
FIG. 3 is an elevational view of the seed sorter of FIG. 2 with a portion broken away illustrating the manner in which seeds are sorted according to size.
Figure 4:
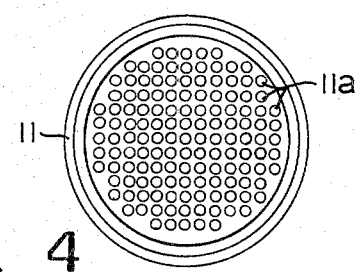
FIG. 4 is a top elevational view of one of the sieves of the seed sorter of FIG. 1.

Each sieve is formed of a cylinder having an open top and a perforated bottom. The perforated bottoms of the sieves 11 through 16 have a plurality of apertures 11a through 16a respectively formed therein. As shown in FIG. 3, the apertures 11a through 16a are formed with decreasing diameters D1 through D6. There is shown in FIG. 4 a top view of sieve 11 which illustrates an example of the placement of the apertures 11a.

The exact number of sieves required to properly sort the seeds is typically dependent on the size variations of the seeds. It has been found that decreasing diameters by one-sixty fourth of inch results in satisfactory seed sorting. Thus, if the seeds ranged in size from 15/64 inch in diameter to 20/64 inch in diameter, diameters D1 through D6 would range from 15/64 inch for D1 to 20/64 inch for D6. In some cases, more sieves may be necessary while, in other cases, a single sieve which sorts the seeds into two groups may be sufficient.

Figure 2:
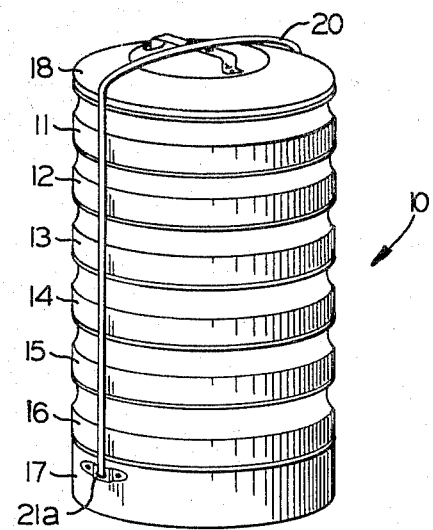
FIG. 2 is a perspective view of the seed sorter of FIG. 1 shown in its assembled condition.

In order to perform the method according to present invention, one first obtains a sample of the type of seeds to be planted. The sorter 10 is then assembled except for the lid 18. The sample of seeds is placed within the uppermost sieve 11. Next, the lid 18 is secured to the sorter 10 by means of the wire closure 20. The entire sorter 10, which is now in the assembled condition as shown in FIG. 2, is then shaken to sort the seeds according to size. FIG. 3 illustrates the manner in which seeds are sorted according to size. Seeds having a diameter larger than the diameter of the apertures in a particular sieve will remain in that sieve. Those seeds which fall into the bottom 17 are smaller than the smallest apertures 16a. The diameter D6 of the apertures 16a is typically chosen sufficiently small such that only reject seeds or weed seeds will fall into the bottom 17.

After the sorter has been shaken to sort the entire sample, the sorter 10 is disassembled. At this time, the user can utilize one of two methods to determine the average number of seeds per pound, depending upon whether he has a weighing scale available. If the user does not have access to a weighing scale, he can use the hand count method. The following table, Table I, will be utilized to illustrate the hand count method.

TABLE I

| | No. of Seeds per Sieve | | Avg. No. Seeds per lb. | | lbs. per Sieve |
|---|---|---|---|---|---|
| Sieve 11 | 0 | ÷ | 1641 | = | .0000 |
| Sieve 12 | 2 | ÷ | 1792 | = | .001 |
| Sieve 13 | 58 | ÷ | 2182 | = | .027 |
| Sieve 14 | 85 | ÷ | 2593 | = | .033 |
| Sieve 15 | 88 | ÷ | 3105 | = | .028 |
| Sieve 16 | 40 | ÷ | 3656 | = | .011 |
| Seed Total = | 273 | | Sample Weight = | | 0.100 lb. |

$$\frac{\text{Seed Total}}{\text{Sample Weight}} = \frac{273}{0.100} \frac{\text{(Seeds)}}{\text{(lb.)}} = 2730 \text{ Seeds per lb.}$$

According to this method, the user first counts the number of seeds which have been sorted into each sieve. This data is entered into the first column under "No. of Seeds per Sieve" and then totalled to obtain the "Seed Total" for the sample. Each of the sieve count values is then divided by a predetermined constant representing the average number of seeds per pound for a particular seed size. These predetermined constants can be obtained from previously conducted agricultural studies, or from research previously conducted by the user himself. The resulting quotient from each of these division operations will represent the weight of the seeds found in each sieve. These individual weighs can then be totalled to obtain the "Sample Weight" of the entire seed sample.

Once the sample weight and the seed total have been determined, the average number of seeds per pound can be calculated. This calculation is shown at the bottom of Table I as the seed total divided by the sample weight.

If the user has access to a weighing scale, he can use the second method, or the weighing method, in order to determine the average number of seeds per pound. The weighing method does not require the user to individually count the number of seeds in the sample. The following table, Table II, will be utilized to illustrate the weighing method.

TABLE II

| | Wt. per Sieve | | Avg. No. Seeds per lb. | | Avg. No. Seeds per Sieve |
|---|---|---|---|---|---|
| Sieve 11 | 0.000 lb. | × | 1641 | = | 0 |
| Sieve 12 | 0.001 | × | 1792 | = | 2 |
| Sieve 13 | 0.027 | × | 2182 | = | 59 |
| Sieve 14 | 0.033 | × | 2593 | = | 86 |
| Sieve 15 | 0.028 | × | 3105 | = | 87 |
| Sieve 16 | 0.011 | × | 3656 | = | 40 |
| Sample Weight = | 0.100 lb. | | Seed Total = | | 274 |

$$\frac{\text{Seed Total}}{\text{Sample Weight}} = \frac{274}{0.100} \frac{\text{(Seeds)}}{\text{(lb.)}} = 2740 \text{ Seeds per lb.}$$

According to the weighing method, a weighing scale is utilized to determine the weight of the seeds which have been sorted into each sieve. This data is entered into the first column under "Weight per Sieve" and then totalled to obtain the "Sample Weight" for the sample. Each of the sieve weights is then multiplied by the respective predetermined constant representing the average number of seeds per pound for a particular seed size. The product of this multiplication results in a value representing the average number of seeds per pound per sieve. When all of these averages have been calculated, they can be totalled to obtain the average number of seeds per pound. If the scale reads in units other than pounds, the total can be converted by applying the appropriate conversion factor. For example, if the total is in grams, the total can be multiplied by the number of grams per pound to obtain the average number of seeds per pound for the seeds to be planted.

In summary, the method according to the present invention comprises the steps of obtaining a random sample of seeds from the quantity of seeds to be planted, sorting the sample into a predetermined number of size ranges, determining a characteristic for each size range, applying an associated constant to each characteristic to obtain a value for each size range, and combining the values to obtain the number of seeds per unit weight. The constants are the average number of seeds per unit weight in each size range. When the steps are performed in accordance with the hand count alternative, the characteristics are numbers of seeds in each size range in the sample, the values are obtained by dividing the characteristics by the constants, and the values are combined by summing them and dividing the sum into the number of seeds in the sample to obtain the number of seeds per unit weight. When the steps are performed in accordance with the weighing alternative, the characteristics are the weight of seeds in each size range in the sample, the values are obtained by multiplying the characteristics by the constants, and the values are combined by summing the values and dividing the sum by the total weight of the sample to obtain the number of seeds per unit weight.

In accordance with the provisions of the patent statutes, the principle and mode of operation of the invention have been explained in its preferred embodiment. However, it must be understood that the invention may be practiced or otherwise than as specifically illustrated and described without departing from its spirit or scope.

What is claimed is:

1. A method of determining the number of seeds per unit weight of a quantity of seeds of various sizes, comprising the steps of:
    a. obtaining a random sample of seeds from the quantity of seeds;
    b. sorting said sample of seeds into a predetermined number of size ranges;
    c. determining a characteristic of the seeds in each of said size ranges;
    d. applying an associated constant to each of said characteristics to obtain a value for each of said size ranges;
    e. combining said values to obtain the number of seeds per unit weight for the quantity of seeds.

2. A method according to claim 1 wherein said step b. is performed by passing said sample of seeds through a plurality of sieves, each successive sieve having openings therein which are smaller in size than the preceding one of said sieves.

3. A method according to claim 1 wherein said step c. is performed by counting the seeds in each of said size ranges to obtain a number as the characteristic of said size range.

4. A method according to claim 3 wherein said step d. is performed by dividing the number of seeds in each of said size ranges as determined in said step c. by said associated constant, representing the average number of seeds per unit weight in each of said size ranges, to obtain said values as total weight per size range.

5. A method according to claim 4 wherein step e. is performed by summing said values obtained in said step d. to obtain a value representing the weight of said sample and dividing the number of seeds obtained in said step c. by said sample weight to obtain the average number of seeds per unit weight for the quantity of seeds.

6. A method according to claim 1 wherein said step c. is performed by weighing the total number of seeds in each of said size ranges to obtain said characteristics as a weight per size range.

7. A method according to claim 6 wherein said step d. is performed by multiplying the weights obtained in said step c. by said associated constants, representing an average number of seeds per unit weight in each of the associated size ranges, to obtain said values as the average number of seeds per size range.

8. A method according to claim 7 wherein said step e. is performed by adding the values obtained in step d. to obtain a sum representing the number of seeds in the sample and dividing said number by the sample weight to obtain the average number of seeds per unit weight for the quantity of seeds.

* * * * *

UNITED STATES PATENT AND TRADEMARK OFFICE
CERTIFICATE OF CORRECTION

PATENT NO.   : 4,381,669
DATED        : May 3, 1983
INVENTOR(S)  : Roger L. Peters It is certified that error appears in the above-identified patent and that said Letters Patent are hereby corrected as shown below:

Column 2, line 43, change "15/64" to --20/64--; and
Column 2, line 44, change "20/64" to --15/64--.

Signed and Sealed this

Ninth Day of August 1983

[SEAL]

Attest:

Attesting Officer

GERALD J. MOSSINGHOFF
Commissioner of Patents and Trademarks